United States Patent
Behl

(10) Patent No.: US 7,727,163 B2
(45) Date of Patent: Jun. 1, 2010

(54) METHODS AND APPARATUS FOR HOLLOW BODY STRUCTURE RESECTION

(75) Inventor: Robert S. Behl, Palo Alto, CA (US)

(73) Assignee: Percutaneous Systems, Inc., Palo Alto, CA (US)

( * ) Notice: Subject to any disclaimer, the term of this patent is extended or adjusted under 35 U.S.C. 154(b) by 1170 days.

(21) Appl. No.: 10/951,922

(22) Filed: Sep. 27, 2004

(65) Prior Publication Data

US 2006/0074436 A1  Apr. 6, 2006

(51) Int. Cl.
*A61B 10/00* (2006.01)

(52) U.S. Cl. ............................ 600/562; 604/11; 600/573

(58) Field of Classification Search ............. 604/11–18, 604/110, 113–115, 358, 362, 364–366; 623/23.72, 623/23.73, 23, 74; 600/562, 564, 572, 573, 600/574

See application file for complete search history.

(56) References Cited

U.S. PATENT DOCUMENTS

| | | | |
|---|---|---|---|
| 3,168,092 A | 2/1965 | Silverman | |
| 3,421,509 A | 1/1969 | Fiore | |
| 3,589,356 A | 6/1971 | Silverman | |
| 4,043,345 A | 8/1977 | Kramann et al. | |
| 4,222,380 A | 9/1980 | Terayama | |
| 4,958,621 A | 9/1990 | Topel et al. | |
| 5,074,840 A * | 12/1991 | Yoon ............................ 604/15 |
| 5,263,927 A | 11/1993 | Shlain | |
| 5,290,310 A * | 3/1994 | Makower et al. ............ 606/213 |
| 5,704,925 A | 1/1998 | Otten et al. | |
| 5,792,114 A | 8/1998 | Fiore | |
| 5,908,429 A | 6/1999 | Yoon | |
| 5,931,810 A | 8/1999 | Grabek | |
| 6,007,521 A | 12/1999 | Bidwell et al. | |
| 6,123,665 A | 9/2000 | Kawano | |
| 6,217,569 B1 | 4/2001 | Fiore | |
| 6,312,421 B1 | 11/2001 | Boock | |
| 6,485,409 B1 | 11/2002 | Voloshin et al. | |
| 6,535,764 B2 | 3/2003 | Imram et al. | |
| 6,585,721 B2 | 7/2003 | Fiore | |
| 6,602,218 B2 * | 8/2003 | Yoon ............................ 604/1 |
| 6,663,594 B2 | 12/2003 | Sahatjian et al. | |
| 6,685,628 B2 | 2/2004 | Vu | |
| 6,706,000 B2 | 3/2004 | Perez et al. | |
| 6,908,428 B2 | 6/2005 | Aizenfeld et al. | |
| 6,988,988 B2 | 1/2006 | Voloshin et al. | |
| 7,328,707 B2 * | 2/2008 | Durgin ........................ 128/887 |
| 2001/0044595 A1 | 11/2001 | Reydel et al. | |
| 2003/0105488 A1 | 6/2003 | Chu | |
| 2003/0196670 A1 | 10/2003 | Durgin | |

OTHER PUBLICATIONS

International Search Report and Written Opinion of PCT Application No. PCT/US05/34533, Dated May 28, 2008, 14 pages total.

\* cited by examiner

*Primary Examiner*—Todd E Manahan
*Assistant Examiner*—Jennifer L Hornberger
(74) *Attorney, Agent, or Firm*—Townsend and Townsend and Crew LLP

(57) ABSTRACT

A body structure is manipulated by first introducing a bulking material, such as a length of material, into an interior of the body structure in either open or laparoscopic surgical procedures. After the bulking material is introduced, an exterior region of the body structure may be manipulated while the material remains within the interior of the body structure. Typically, manipulation comprises resection of the body structure from surrounding tissue. The resected body structure may then be removed.

60 Claims, 9 Drawing Sheets

METHODS AND APPARATUS FOR HOLLOW BODY STRUCTURE RESECTION

BACKGROUND OF THE INVENTION

1. Field of the Invention

The present invention relates generally to medical methods and devices. More particularly, the present invention relates to methods and systems for stabilizing hollow body structures during manipulation such as resection.

The removal of hollow body structures can be difficult because of their delicate structure. The difficulty can be exacerbated when the hollow body structure is filled with fluids and/or is firmly attached to surrounding tissues. The removal of fluid-filled cysts, especially those on the kidneys, spine, ovaries, liver, and the gastro-intestinal tract, can be particularly difficult since accidental loss of the fluid presents a number of problems. In addition to releasing potentially toxic and carcinogenic materials, loss of the cyst fluid causes the cyst to lose its shape and inhibits visualization. The remaining loose "sack" structure can be very difficult to remove, particularly in laparoscopic procedures where access is limited. Finally, loss of fluid from the cyst can make subsequent examination of the fluid difficult since it will have become contaminated with other tissues and fluids in the body.

For these reasons, it would be desirable to provide improved methods, systems, and apparatus for manipulating cysts and other hollow body structures in both minimally invasive and open surgical procedures. It would be particularly desirable if the body structures could be stabilized in order to both reduce the risk of accidental loss of internal fluids and stabilize the exterior of the body structure to facilitate resection and subsequent removal. For laparoscopic and other minimally invasive procedures, it would be further desirable to be able to dissect the body structure into smaller pieces to facilitate removal through a cannula or other access tube. At least some of these objectives will be met by the inventions described herein below.

2. Description of the Background Art

Apparatus and methods for accessing and/or injecting materials into various hollow and other body structures are described in U.S. Pat. Nos. 4,222,380; 4,958,621; 5,263,927; 5,704,925; 5,908,429; 5,931,810; 6,123,665; 6,312,421; 6,663,594; 6,685,628; 6,706,000; and published application US2003/0105488.

BRIEF SUMMARY OF THE INVENTION

The present invention provides improved methods, apparatus, and systems for accessing, stabilizing, and manipulating a variety of hollow and other body structures, particularly including fluid-filled body structures, such as cysts. The cysts may be found on a variety of organs, including the kidneys, the spine, the ovaries, the liver, the gastro-intestinal tract, and the like. Other exemplary body structures which may be manipulated according to the present invention include the intestines, the bladder, the gallbladder, and the like.

Manipulation according to the present will usually include resection and removal of the body structure, optionally further including dissection of the structure prior to removal. The present invention would find use, however, with many other protocols which might benefit from stabilization of the body structure during a subsequent manipulation.

The present invention relies on the ability to physically fill and stabilize a body structure with a bulking material, including both solid bulking materials, typically in the form of a length of material, and non-solid bulking materials, typically in the form of a fluid which gels or otherwise hardens to stabilize the body structure. Such stabilization can reduce the risk of loss of native fluids from cysts and other fluid-filled body structures. Additionally, such stabilization improves the ability of a surgeon to manipulate and dissect the body structure from surrounding tissue, particularly in laparoscopic and other minimally invasive procedures. The methods, however, will also be useful in open surgical procedures.

In a first aspect of the present invention, a method for manipulating a body structure comprises introducing at least one length of material through at least one exterior site and into an interior of the body structure. The length of material will occupy at least a portion of the interior, acting to prevent collapse of the structure and facilitate subsequent manipulation of an exterior region of the body structure. Optionally, if fluids are initially present in the body structure, the length of material may absorb the native fluids to prevent accidental loss should the exterior of the body structure become damaged. Further optionally, the length of material may be left intact and a free end outside of the body structure used to hold and help manipulate the structure. Alternatively, the material may be (at or near the surface of the cover) body structure to allow removal of an access tube and/or a dispensing tube used to deploy the material, as described below.

The body structure will usually be accessed by positioning an access tube to penetrate the structure at the exterior site to provide an access passage through the access tube to the interior of the body structure. More usually, the access tube will be able to seal to the body structure to prevent leakage of fluid or any other substance from the interior of the body structure. Access may be effected in a variety of ways. For example, the exterior region may be plicated, typically by clamping the exterior region between opposed elements where the opposed elements usually have atraumatic interface surfaces which engage the exterior region. The access member may then be advanced into the plicated exterior region while it remains immobilized by the clamp. Alternatively, a vacuum may be applied over the exterior region, typically through the access tube itself. The vacuum can immobilize the exterior while it is penetrated by the access tube.

Once the access tube is in place, the at least one length material may be delivered through the access tube into the interior and the body structure. The length of material may be introduced directly through the access tube, for example by manually advancing it. More usually, over, the length of material will be dispensed through a separate dispensing tube which is positioned through the access tube. The separate dispensing tube may include manual or powered means for advancing the length of material until a desired portion of the interior of the body structure is filled, typically filling substantially the entire interior of the hollow body structure.

Usually, only a single continuous length of the material will be delivered into the interior of the body structure. This facilitates optional subsequent withdrawal of the length of material since there is only one length to remove. Alternatively, however, it is possible to introduce two or more lengths of materials, either simultaneously or sequentially and either through the same access tube or through separate access tubes. For example, in the case of irregularly shaped body structures, it may be desirable to access two different regions of the structure to separately introduce lengths of material which would be difficult to introduce through a single site.

The access tube may be positioned under direct imaging, such as using a laparoscope, endoscope, or similar visualization equipment. Alternatively or additionally, the access tube may be positioned under fluoroscopic or other indirect imaging systems.

After the length of material has been introduced and the body structure freed from adjacent tissues, it might be desirable to withdraw at least a portion of the length of material, for example to facilitate sectioning and removal of the body structure through the access tube or other cannula having a limited lumen size. Usually, the entire length (or lengths) of material will be completely withdrawn prior to resection. Most simply, withdrawing may comprise pulling on a free end of the length(s) of material and withdrawing, typically through the same access cannula or other tube which was used to introduce the material. Withdrawing the material prior to disruption of the body structure is also advantageous since fluids absorbed by the material can then be analyzed, for example by chemical, histochemical, and/or cytological analyses to help diagnose the patient's condition.

As described above, manipulating will frequently comprise resecting the body structure, i.e. separating at least a portion of the exterior of the body structure from surrounding tissue. Conveniently, such resection and separation may be performed by manipulating the access tube to apply traction on the body structure. The use of other resection instruments introduced through the same or different access sites may of course also find use. When removing the body structure, the exterior of the body structure will usually be completely dissected from surrounding tissue. After such complete resection, and optionally removal of the length(s) of material, the body structure may be sectioned into smaller pieces and the pieces then removed, typically through a trocar or port, which in some instances may be the same access tube which was used to introduce the length(s) of material.

The material which is introduced will typically comprise a liquid absorptive, such as a fabric, a hydrogel, or other material which is capable of absorbing and sequestering any liquid, fluid, or other materials present in the interior of the body structure. In the case of hydrogels, the length(s) of material may further comprise a reinforcement component extending at least over a portion of its length. The reinforcement component may be used to facilitate withdrawal of the material after the manipulation is complete.

Alternatively, the continuous length of material may comprise or consist of a material which does not absorb liquid. In such cases, when a fluid is initially present in the body structures, it will often be desirable to at least partially aspirate the fluid from the interior of the body structure prior to introducing the non-absorptive length of material. Of course, in some instances, it may be desirable to introduce a combination of both absorptive and non-absorptive lengths of materials, for example in order to adjust the consistency of the body structure when filled with the material.

In a second aspect, the methods of the present invention for manipulating a body structure comprise introducing a bulking material into an interior of the body structure, manipulating an exterior region of the body structure while the bulking material remains present, and withdrawing at least a portion of the bulking material after manipulating the exterior region. The bulking material may be a solid material, such as the lengths of material as described above, or may be a non-solid material, such as a fluid, gel, or liquid which is capable of hardening or solidifying within the body structure in order to provide a desired level of stabilization. Exemplary non-solid bulking materials include hydrophilic substances, such as gels, foams, and the like, which will react with water and aqueous substances within the body structure to set or harden in situ. The materials, however, will not necessarily completely harden since they may later be removed from the interior of the body structure, typically using a vacuum or other aspiration system.

Such bulking materials will typically be introduced into the interior of the body structure using an access tube in a manner as described above in connection with the first methods of the present invention. After the bulking materials are introduced, and a desired level of stabilization achieved, the body structure may be manipulated, typically being resected and separated from the surrounding tissue. The body structure may also be removed, typically by sectioning, again as described with respect to the first methods of the present invention.

In a third aspect, the present invention provides apparatus for accessing a body structure. The apparatus includes means for immobilizing an exterior region of the body structure without rupturing said structure. A tubular access member is adapted to be advanced relative to the immobilizing means to penetrate the immobilized exterior region, preferably without significant leakage of the contents, and means for injecting a bulking material through the access member to deliver the bulking material into an interior of the body structure. The immobilizing means will usually comprise a shaft having a distal end and a proximal end. A clamp may be provided at the distal end of the shaft having opposed elements adapted to altraumatically grasp the exterior of the body structure. The opposed elements are usually in the form of a jaw, and the jaw will usually have atraumatic surfaces which engage the exterior of the body structure to reduce the risk of injury. Alternatively, the immobilizing means may comprise a vacuum port or ports at the distal end of the shaft, where the port(s) are adapted to engage and secure a portion of the exterior surface of the body structure. For example, a port may comprise a cone having an interior for applying the vacuum an in atraumatic distal tip or edge for engaging the exterior of the body structure. The cone may further be capable of shifting between a small diameter configuration for introduction through tissue and a large diameter configuration for engaging the membrane.

The tubular access member will usually be mounted to axially reciprocate relative to the shaft and through the interior of either the jaw structure, the core, or other immobilization structure on the shaft. The tubular access member will typically be a cannula or other similar structure having a self-penetrating tip, such as a sharpened distal end.

In a first embodiment of the apparatus, the injecting means will be adapted to advance a length of material through the access member. Usually, the injecting means will further comprise means for selectively severing the length of the material so that the physician may cut the material after the interior of the body structure has been filled to a desired degree. Further, the injecting means will usually include means for recapturing a severed end of the length of the material to facilitate removal of the material after the body structure has been manipulated.

In a second embodiment of the apparatus, the injecting means will be adapted to advance, inject, or otherwise introduce a fluid bulking material through the access member. A syringe or similar mechanism may be utilized.

DETAILED DESCRIPTION OF THE INVENTION

Figure 1:
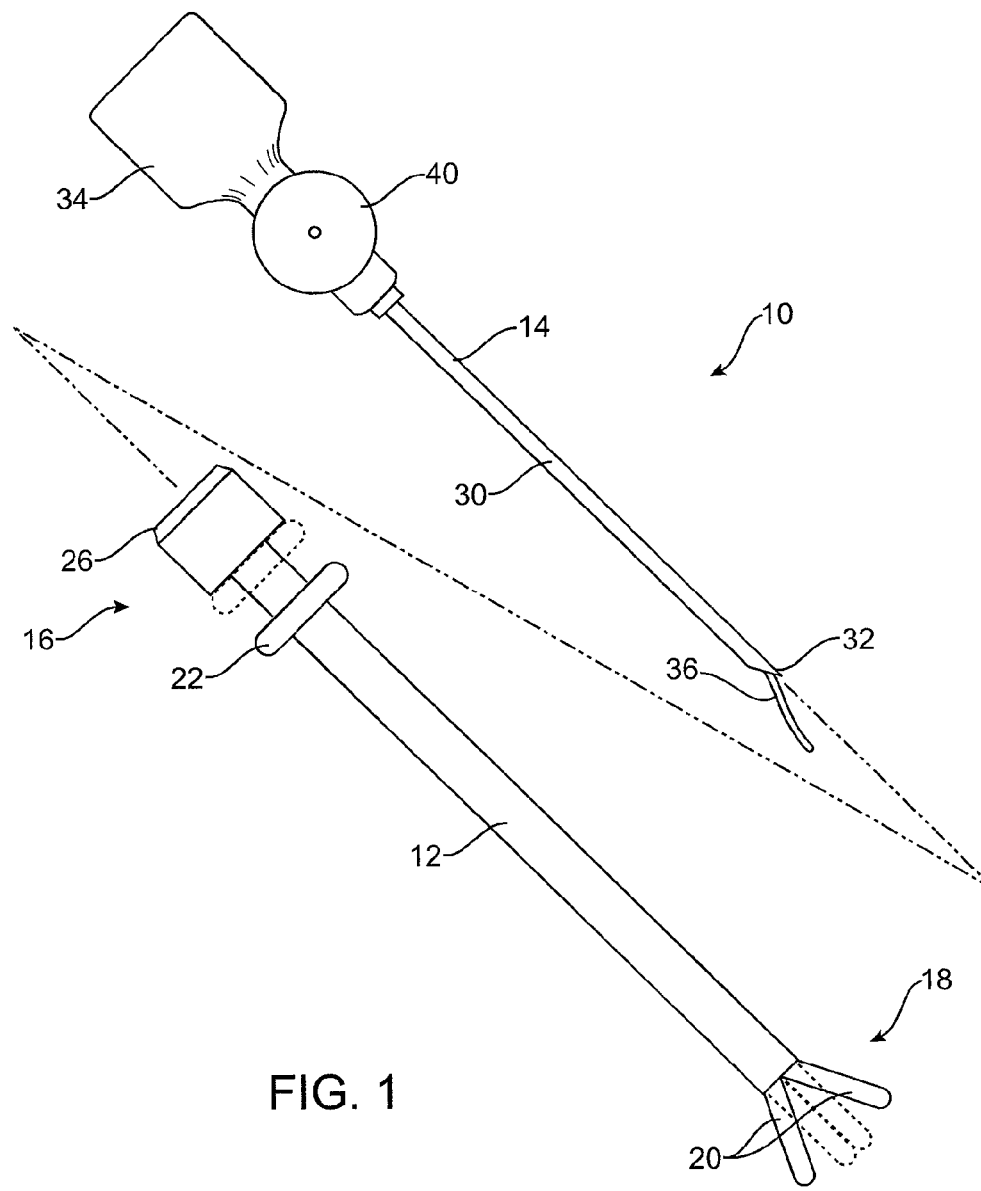
FIG. 1 illustrates an exemplary apparatus comprising an access tube and material introduction device constructed in accordance with the principles of the present invention.

An exemplary system 10 for manipulating a body structure in accordance with the principles of the present invention comprises an access tube 12 and a material injector 14 which is adapted to be introduced through the access tube 12. An access tube has a proximal 16 and a distal end 18. A pair of atraumatic jaws 20 are pivotally attached at the distal end 18 and can be opened and closed using a slider mechanism 22 near the proximal end of the access tube 12. The slider may be attached to, for example, one or more cables, shafts, or pull wires which are able to open and close the jaws between the open configuration shown in full line and the close configuration shown in broken line in FIG. 1. The slider would be simply retracted from the position shown in full line to the position shown in broken line to accomplish such closure. The access tube 12 further includes a pneumostatic port 26, also at its proximal end, for permitting the introduction of the material injector 14 into the access tube while the access tube is present in a region, such as an insufflated peritoneum as described hereinbelow.

The material injector 14 comprises a shaft 30 having a sharpened distal tip 32 or other introducing element at its distal end. A proximal handle 34 may be provided to carry the length of material 36 which is to be introduced through the distal end of the shaft 30, as will be described in more detail below. The length of material stored in the handle 34 may be advanced using a conventional mechanism, such as a thumb wheel 40 which may be manually rotated to engage and advance the length of material so that it passes out of the tip 32 into the interior of the body structure, as described in more detail below. Optionally, the thumb wheel may be connected to a ratchet to permit only advancement of the material length. Further optionally, the ratchet may have a switch which permits selection of advancement or retraction using the thumb wheel.

It will be appreciated that a variety of other designs could be utilized for the material injector. For example, when using non-solid bulking materials, it could be possible to use a syringe or other conventional fluid injector. In all instances, the injector may be provided with a motor or other pneumatic, electrical, or other powered drive in order to permit automatic or controlled delivery of the bulking material.

Figure 2:
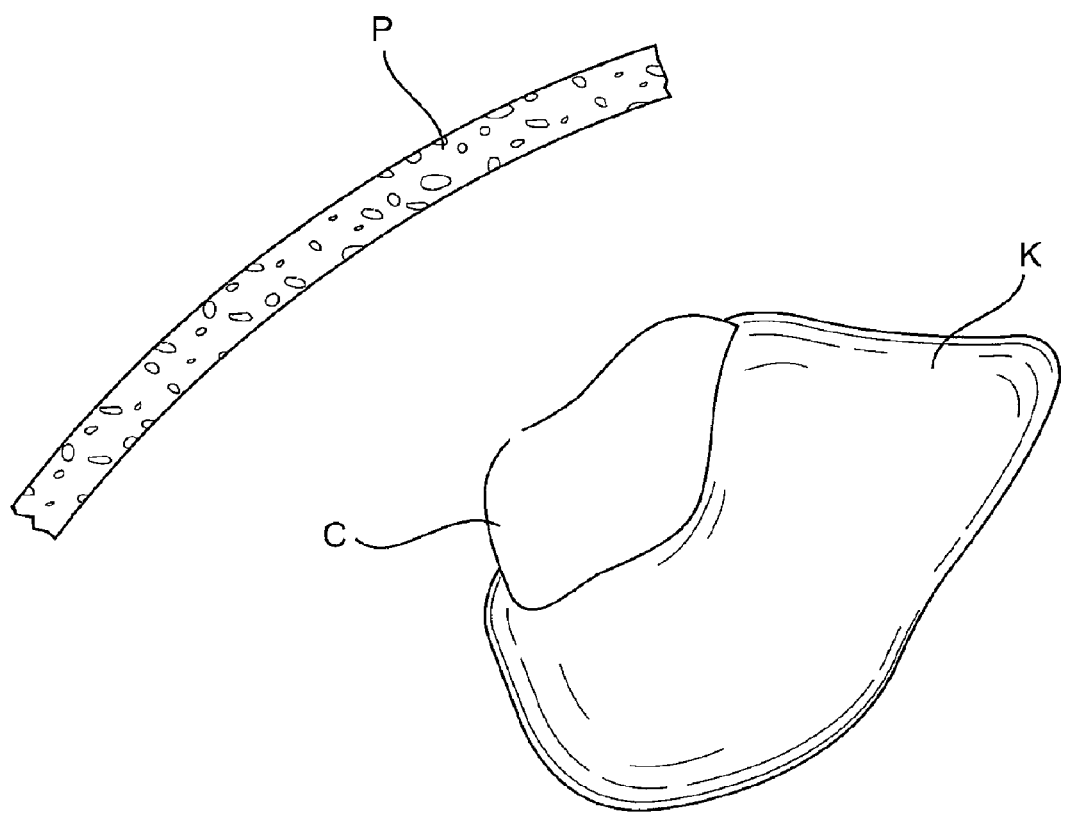
FIGS. 2 through 9 illustrate use of the apparatus of FIG. 1 for introducing a length of material into a fluid-filled cyst to facilitate resection and removal in accordance with the principles of the present invention.
Figure 3:
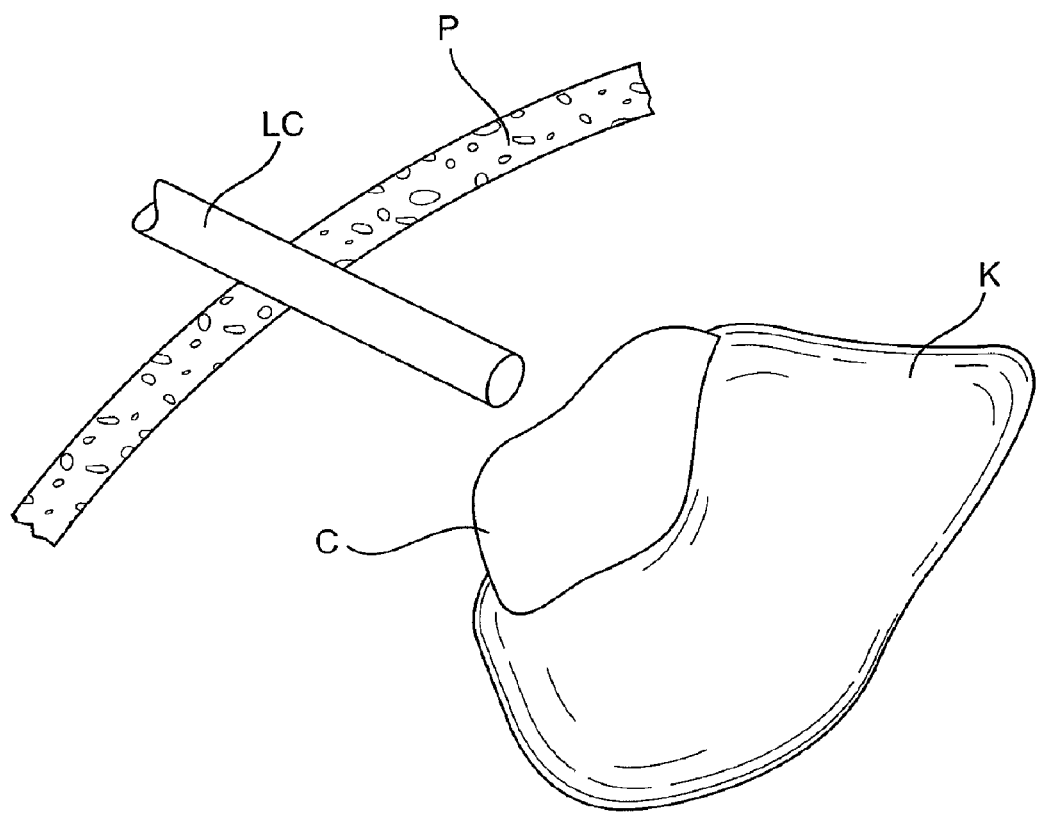
Figure 4:
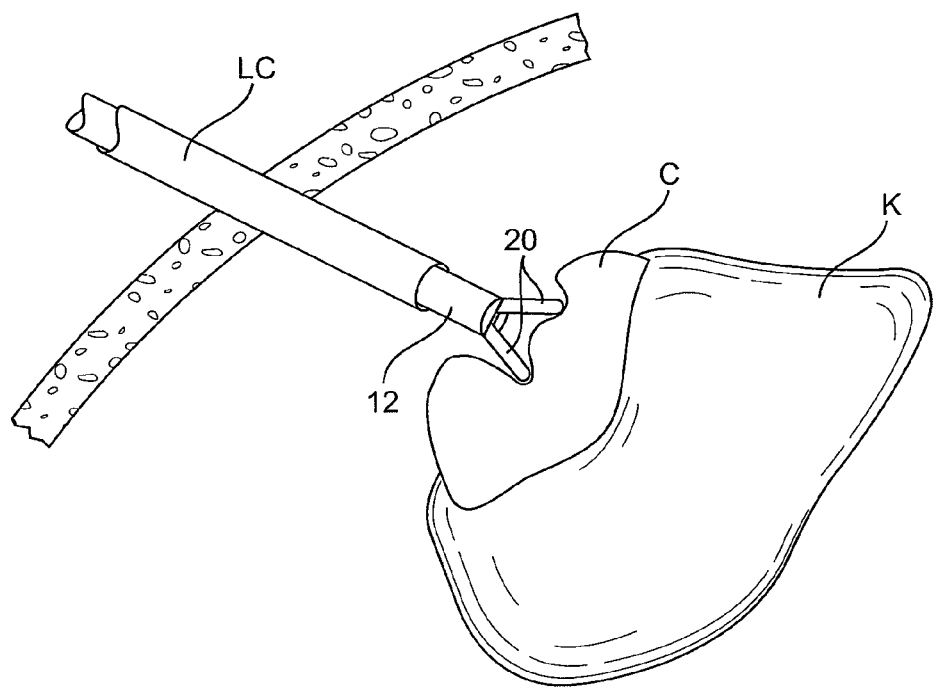
Figure 5:
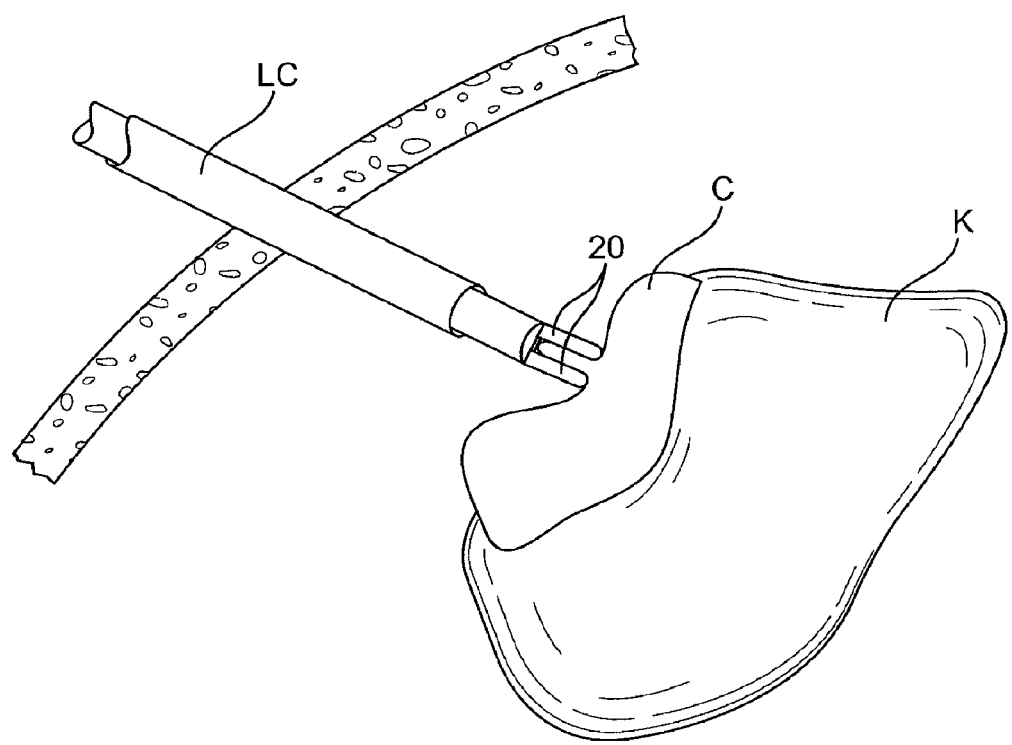
Figure 6:
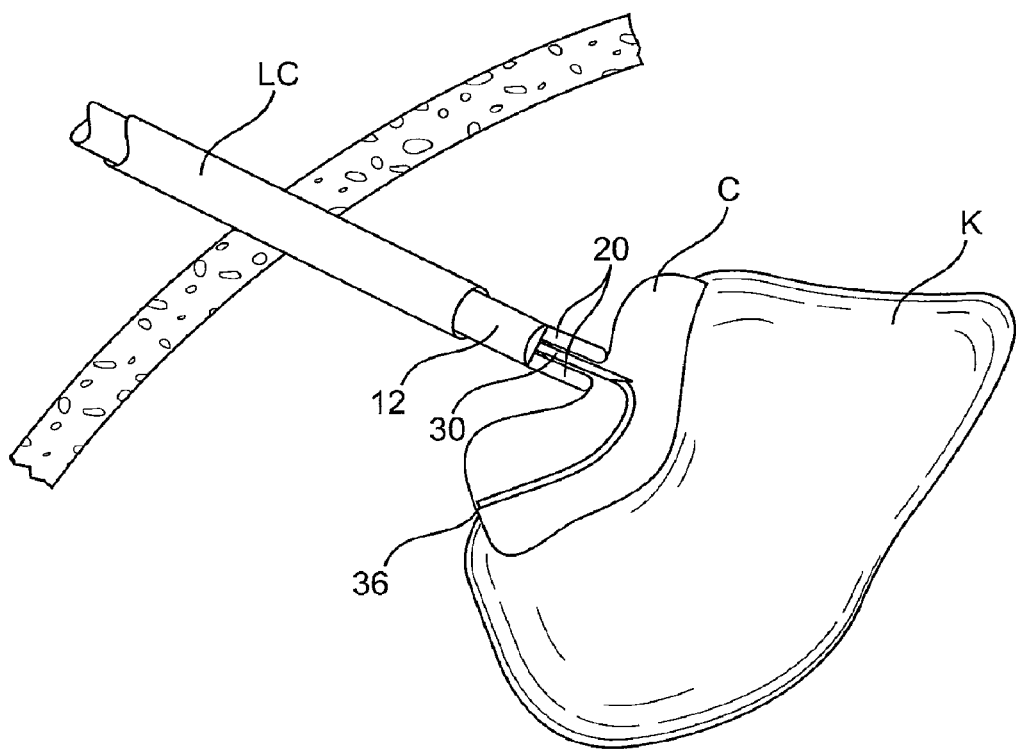
Figure 7:
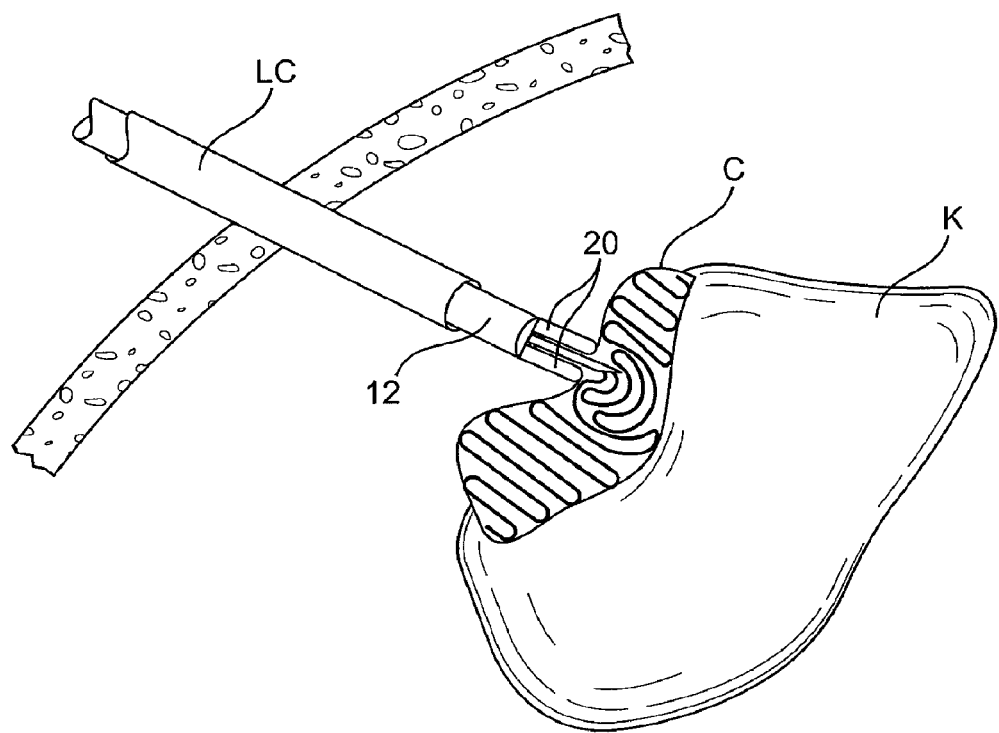
Figure 8:
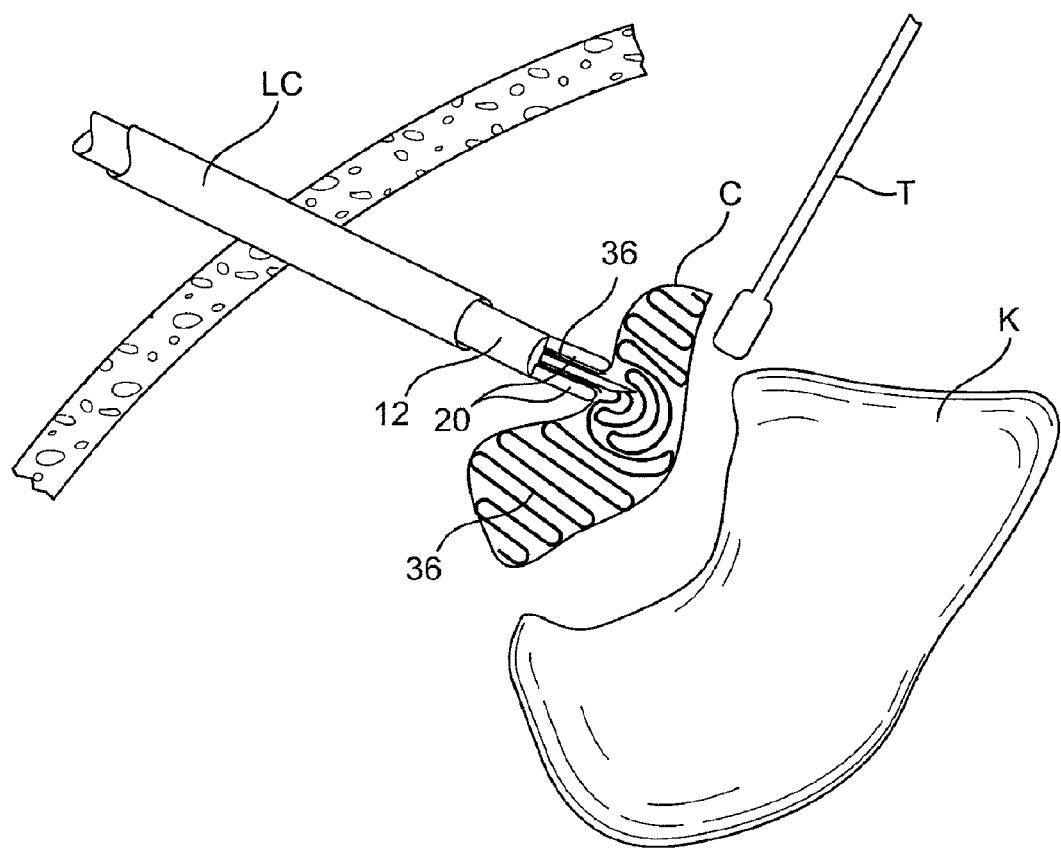
Figure 9:
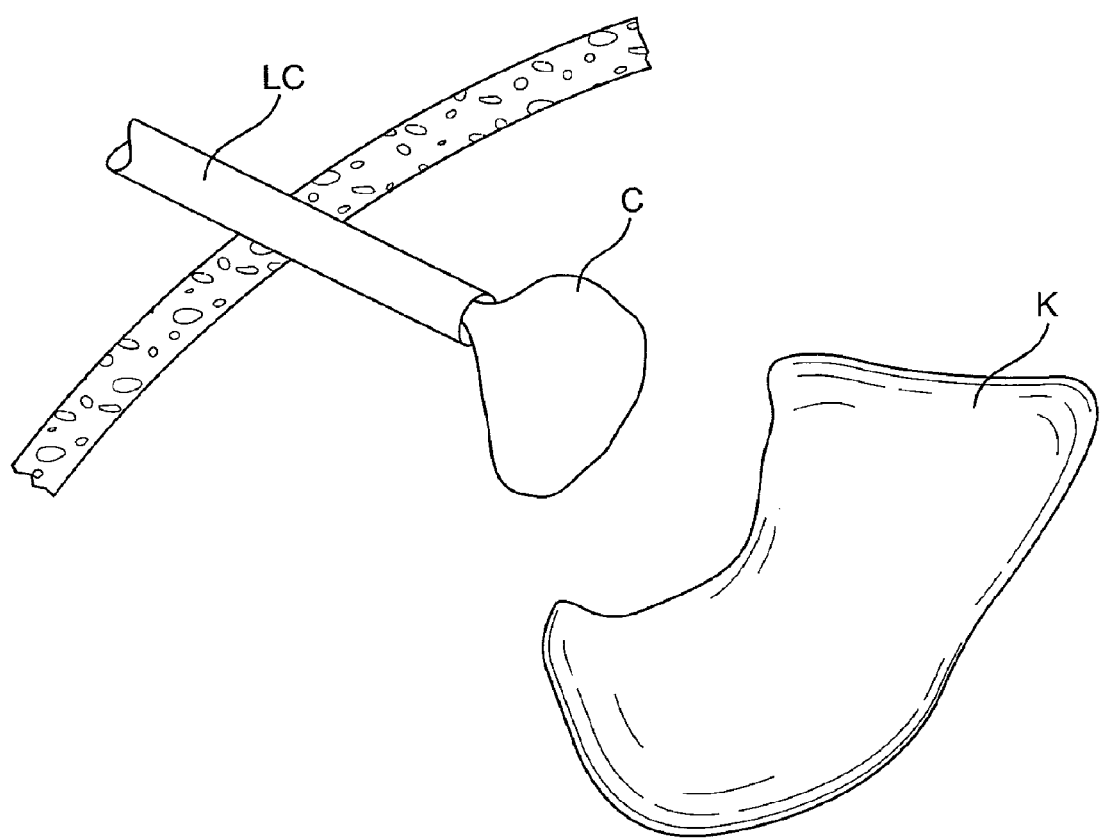

Referring now to FIGS. 2-9, an exemplary method utilizing the system 10 for injecting a length of a material in accordance with the principles the present invention into a fluid-filled cyst C will be described. Referring in particular to FIG. 2, the fluid-filled cyst C may be present on a kidney K which may be accessed using a variety of techniques, including both laparoscopic techniques and surgical (not shown). Shown in FIG. 3, the patient's peritoneum P may be insufflated in order to provide an access region above the cyst C. A conventional laparoscopic or other cannula LC may be introduced through the patient's abdomen above the cyst C. As shown in FIG. 4, the access tube 12 is introduced through the laparoscopic cannula LC, and jaws 20 then opened over the cyst C. As shown in FIG. 5, the jaws 20 may be closed to altraumatically grasp an exterior region of tissue on the cyst C. After the exterior region of the cyst C has been immobilized (FIG. 6), the shaft 30 is introduced into the interior of the cyst, and the length of material 36 may then be advanced. Optionally, prior to advancing the length of material, a portion of the fluid within the cyst could be aspirated for subsequent analyses. The length of material continues to be advanced until the cyst is completely filled, as shown in FIG. 7. Optionally, the length of material will be absorptive so that the fluid is sequestered and stabilized within the material filling the cyst. The cyst C may then be resected from the kidney K, optionally using a separate resection tool T, as shown in FIG. 8. Resection and separation of the intact cyst can be accomplished by a controlled manual traction applied using the access tube 12 which continues to grasp the cyst. During resection, the length of material preferably remains within the cyst in order to continue to provide stabilization. After the cyst has been fully resected, the length of the material may be withdrawn to deflate the cyst, and the access tube may be retracted, drawing the cyst into the laparoscopic cannula LC as shown in FIG. 9. Optionally, the cyst could be sectioned into two or more pieces prior to facilitate withdrawal through the laparoscopic cannula LC or other removal.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for manipulating a cyst body structure, said method comprising:
    penetrating an access tube through an exterior wall of the cyst body structure, wherein said access tube seals to the cyst body structure to produce a passage into an interior of the cyst body structure while preventing leakage therefrom;
    introducing at least one length of material through the passage of said access tube into the interior of the cyst body structure to substantially fill the entire interior of the cyst body structure; and
    manipulating an exterior region of the cyst body structure while said length of material remains within the interior of the cyst body structure;
    wherein manipulating comprises separating at least a portion of the exterior of the cyst body structure from surrounding tissue while said length of material remains within the interior of the cyst body structure.

2. A method as in claim 1, wherein introducing comprises advancing a single continuous length of material until a sufficient amount has been introduced into the interior of the cyst body structure.

3. A method as in claim 2, wherein the access tube is positioned under direct imaging.

4. A method as in claim 2, wherein the access tube is positioned under indirect imaging.

5. A method as in claim 1, wherein introducing comprises advancing two or more lengths of material.

6. A method as in claim 5, wherein the two or more lengths of material are introduced sequentially through the same passage into the interior of the cyst body structure.

7. A method as in claim 5, wherein the two or more lengths of material are introduced simultaneously through the same passage into the interior of the cyst body structure.

8. A method as in claim 1, wherein introducing further comprises advancing the access tube into a plicated region of the exterior wall.

9. A method as in claim 8, wherein introducing comprises plicating the exterior wall.

10. A method as in claim 9, wherein plicating comprises clamping the exterior wall between opposed elements.

11. A method as in claim 10, wherein the opposed elements have atraumatic interface surfaces which engage the exterior wall.

12. A method as in claim 1, wherein introducing comprises applying a vacuum over the exterior wall.

13. A method as in claim 12, wherein the vacuum is applied through the access tube.

14. A method as in claim 1, further comprising dispensing the length of material using a dispensing tube positioned in the access tube.

15. A method as in claim 14, wherein dispensing comprises advancing a thumb wheel using one hand.

16. A method as in claim 15, wherein the thumb wheel can advance but not retract the length of material.

17. A method as in claim 1, wherein the length of material is introduced directly through the access tube without a dispensing tube.

18. A method as in claim 1, further comprising withdrawing at least a portion of the length of material after manipulation of the exterior region.

19. A method as in claim 18, wherein all lengths of material are completely withdrawn.

20. A method as in claim 18, wherein withdrawing comprises pulling on a proximal end of the length(s) of material.

21. A method as in claim 18, wherein the portion of material removed is sufficient to perform an analysis.

22. A method as in claim 21, further comprising performing a chemical, histochemical and/or cytological analysis on the removed length of material.

23. A method as in claim 1, wherein further comprising manipulating the access tube which remains attached to the cyst body structure.

24. A method as in claim 23, wherein manipulating comprises applying tension to the cyst body structure while the cyst body structure is dissected.

25. A method as in claim 24, wherein manipulating comprises dissecting the exterior of the cyst body structure completely from surrounding tissue.

26. A method as in claim 25, further comprising removing the cyst body structure after said structure has been freed from the surrounding tissue.

27. A method as in claim 26, wherein the cyst body structure is sectioned into smaller pieces and the pieces are removed.

28. A method as in claim 27, wherein the pieces are removed percutaneously through the access tube.

29. A method as in claim 28, wherein the pieces are removed through the access tube which had been used to introduce the length of material.

30. A method as in claim 1, wherein the length of material comprises a liquid absorptive component.

31. A method as in claim 30, wherein the liquid absorptive component comprises a hydrogel.

32. A method as in claim 30, wherein the liquid absorptive component comprises a fabric.

33. A method as in claim 30, wherein the length of material comprises a reinforcement component extending over at least most of its length.

34. A method as in claim 1, wherein the length of material does not absorb liquid.

35. A method as in claim 34, wherein a fluid present in the cyst body structure is at least partly aspirated prior to introducing the length of material.

36. A method as in claim 1, further comprising aspirating a fluid from the cyst body structure prior to introducing the length of material.

37. A method as in claim 1, wherein the cyst body structure is on an organ selected from the group consisting of the kidneys, spine, ovary, liver and gastrointestinal tract.

38. A method for manipulating a cyst body structure, said method comprising:
    penetrating an access tube through an exterior region of the cyst body structure, wherein said access tube seals to the cyst body structure to produce a passage into an interior of the cyst body structure while preventing leakage therefrom;
    introducing a bulking material to the interior of the cyst body structure to substantially fill the entire interior of the cyst body structure;
    manipulating the exterior region of the cyst body structure while said bulking material is present; and
    withdrawing at least a portion of the bulking material after manipulating the exterior region;
    wherein manipulating comprises separating at least a portion of the exterior of the cyst body structure from surrounding tissue while said bulking material is present in the interior of the cyst body structure.

39. A method as in claim 38, wherein penetrating the access tube comprises plicating the exterior region and advancing the tube through the plicated region.

40. A method as in claim 39, wherein plicating comprises clamping the exterior region between opposed elements.

41. A method as in claim 40, wherein the opposed elements have atraumatic interface surfaces which engage the exterior region.

42. A method as in claim 40, wherein the access tube is advanced between the opposed elements.

43. A method as in claim 38, wherein further comprising applying a vacuum over the exterior region.

44. A method as in claim 43, wherein the vacuum is applied through the access tube.

45. A method as in claim 38, wherein the bulking material is injected through the access tube.

46. A method as in claim 38, wherein the access tube is positioned under direct imaging.

47. A method as in claim 38, wherein the access tube is positioned under indirect imaging.

48. A method as in claim 38, further comprising tensioning the cyst body structure by drawing on the access tube which remains attached to the cyst body structure while the tissue is separated.

49. A method as in claim 38, wherein manipulating comprises freeing the exterior of the cyst body structure completely from surrounding tissue.

50. A method as in claim 49, further comprising removing the cyst body structure after said structure has been freed from the surrounding tissue and the bulking material withdrawn.

51. A method as in claim 50, wherein the cyst body structure is sectioned into smaller pieces and the pieces are removed.

52. A method as in claim 51, wherein the pieces are removed percutaneously through the access tube.

53. A method as in claim 38, further comprising withdrawing at least a portion of the bulking material after manipulation of the exterior region.

54. A method as in claim 53, wherein the entire volume of material is withdrawn.

55. A method as in claim 38, wherein the bulking material is selected from the group consisting of a gel, a foam, or a hydrophilic substance, selected to sequester any contents of the body structure and inhibit leakage should the structure be damaged during manipulation.

56. A method as in claim 38, wherein the bulking material comprises length of material.

57. A method as in claim 38, further comprising aspirating a fluid from the cyst body structure prior to introducing the bulking material.

58. A method as in claim 57, wherein an amount of the fluid removed is sufficient to perform an analysis.

59. A method as in claim 58, further comprising performing a chemical, histochemical and/or cytological analysis.

60. A method as in claim 38, wherein the cyst body structure is in an organ selected from the group consisting of the kidneys, spine, ovary, liver and gastrointestinal tract.

* * * * *